United States Patent [19]

Platt et al.

[11] 4,041,159

[45] Aug. 9, 1977

[54] NEMATOCIDAL 4-AMINO-N-THIO-SUBSTITUTED 3,5-DINITROBENZENESULFONAMIDES

[75] Inventors: James L. Platt, Novato; William L. Schinski, San Rafael, both of Calif.

[73] Assignee: Chevron Research Company, San Francisco, Calif.

[21] Appl. No.: 657,678

[22] Filed: Feb. 12, 1976

[51] Int. Cl.$^2$ .............................................. A01N 9/16
[52] U.S. Cl. .............................. 424/228; 260/397.7 R
[58] Field of Search .................. 260/397.7 R; 424/228

[56] References Cited

U.S. PATENT DOCUMENTS

| 3,367,949 | 2/1968 | Sopev | 260/397.7 R |
| 3,840,569 | 10/1974 | Beck | 260/397.7 R |
| 3,875,192 | 4/1975 | Suhr | 260/397.7 R |

Primary Examiner—Jerome D. Goldberg
Attorney, Agent, or Firm—J. A. Buchanan, Jr.; Dix A. Newell; Raymond Owyang

[57] ABSTRACT

Compounds of the formula

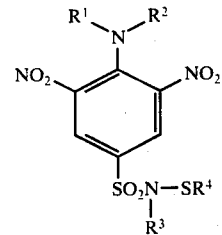

wherein $R^1$, $R^2$ and $R^3$ are alkyl and $R^4$ is alkyl, haloalkyl or aryl.

5 Claims, No Drawings

NEMATOCIDAL 4-AMINO-N-THIO-SUBSTITUTED 3,5-DINITROBENZENESULFONAMIDES

DESCRIPTION OF THE PRIOR ART

U.S. Pat. No. 3,367,949 of Soper discloses the use of 4-dialkylamino-3,5-dinitrobenzenesulfonamides as herbicides.

DESCRIPTION OF THE INVENTION

The nematocidal compounds of the invention are represented by the formula

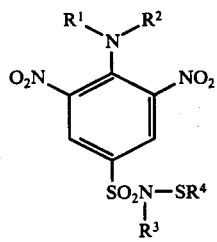

wherein $R^1$ is alkyl of 1 to 6 carbon atoms, $R^2$ is alkyl of 1 to 6 carbon atoms, $R^3$ is alkyl of 1 to 6 carbon atoms and $R^4$ is alkyl of 1 to 6 carbon atoms, haloalkyl of 1 to 2 carbon atoms and 1 to 5 of the same or different halogens selected from fluoro, chloro or bromo, phenyl, phenyl substituted with 1 to 2 of the same or different substitutents selected from fluoro, chloro, bromo or alkyl of 1 to 4 carbon atoms.

Representative haloalkyl $R^4$ groups include fluoromethyl, chloromethyl, dibromomethyl, trichloromethyl, tribromomethyl, tetrachloroethyl, and pentachloroethyl.

Representative aryl $R^4$ groups include 2-fluorophenyl, 3-chlorophenyl, 2,4-dichlorophenyl, 3,4-dibromophenyl, 2-methyl-4-chlorophenyl, 4-methylphenyl and 2,4-dimethylphenyl.

Representative alkyl groups which $R^1$, $R^2$, $R^3$ and $R^4$ may represent include methyl, ethyl, n-propyl, isopropyl, n-butyl, isohexyl, etc. Preferred alkyl groups are those having 1 to 3 carbon atoms, e.g., methyl, ethyl or propyl.

Representative compounds of the invention include
4-dimethylamino-N-methyl-N-trichloromethylthio-3,5-dinitrobenzenesulfonamide,
4-dipropylamino-N-methyl-N-tetrachloroethylthio-3,5-dinitrobenzenesulfonamide,
4-dihexylamino-N-ethyl-N-tolylthio-3,5-dinitrobenzenesulfonamide,
4-diethylamino-N-methyl-N-phenylthio-3,5-dinitrobenzenesulfonamide,
4-methylpropylamino-N-hexyl-N-p-bromophenylthio-3,5-dinitrobenzenesulfonamide,
4-diisopropyl-N-methyl-N-ethylthio-3,5-dinitrobenzenesulfonamide, and
4-dipropyl-N-propyl-N-propylthio-3,5-dinitrobenzenesulfonamide.

The compounds of the invention are prepared by sulfenylating a 4-dialkylamino-N-alkyl-3,5-dinitrobenzenesulfonamide (II) with a sulfenyl halide (III) in the presence of an acid acceptor, as depicted by the following reaction:

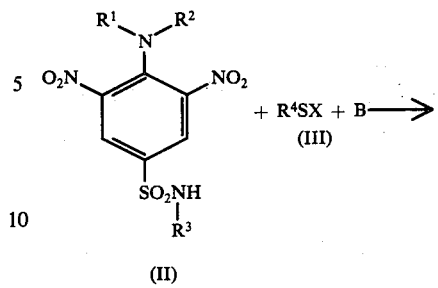

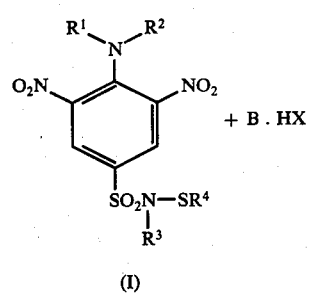

wherein $R^1$, $R^2$, $R^3$ and $R^4$ have the same significance as previously defined, X is chloro or bromo and B is an acid acceptor.

The acid acceptor may be an organic base or an inorganic base. Suitable inorganic bases include alkali and alkaline earth carbonates, e.g., sodium carbonate or calcium carbonate. Suitable organic bases include pyridine compounds, e.g., pyridine or alkylpyridines, and trialkylamines, e.g., triethylamine or tributylamine. The preferred acid acceptors are pyridine compounds, especially pyridine.

Reaction (1) is conducted by more or less conventional procedures. The molar ratio of the benzenesulfonamide (II) to the sulfenyl halide (III) and the molar ratio of the acid acceptor to the sulfenyl halide (III) are substantially equimolar. If desired, however, a small excess of the sulfenyl halide (III) and/or the acid acceptor may be employed. The reaction is conducted in the liquid phase, generally in an inert organic diluent. Suitable inert diluents include alkanes and haloalkanes such as hexane or dichloromethane, and aromatic compounds such as benzene, toluene or chlorobenzene. The reaction temperature suitably varies from about −10° C to 150° C, although a temperature of from about 0° C to 50° C is preferred. The reaction pressure may be atmospheric, subatmospheric or superatmospheric. For convenience, the pressure is usually atmospheric. The reaction is normally completed within 1 to 24 hours. The product is isolated by conventional procedures such as extraction, crystallization, chromatography, etc.

Alternatively, the compounds of the invention may be prepared by reacting a 4-dialkylamino-N-alkyl-3,5-dinitrobenzenesulfonyl halide (IV) with a thioamine (V) in the presence of an acid acceptor, as depicted by the following reaction:

(2)

-continued $$\underset{(IV)}{\text{[structure: benzene ring with } N(R^1)(R^2) \text{, two } O_2N \text{ groups, and } SO_2X\text{]}} + HN(R^3)-SR^4 \rightarrow (I) + B \cdot HX$$

(V)

wherein $R^1$, $R^2$, $R^3$, $R^4$, X and B have the same significance as previously defined.

Reaction (2) is conducted by conventional procedures. Suitable acid acceptors are those employed in Reaction (1). The molar ratio of the benzenesulfonyl halide (IV) to the thioamine (V) and the molar ratio of the acid acceptor to the benzenesulfonyl halide (IV) are substantially equimolar. The reaction is generally conducted in the liquid phase in an inert organic diluent at a temperature of from about $-10°$ C to 100° C. The product is isolated by conventional procedures such as extraction, crystallization, chromatography, etc.

The thioamine reactants (V) may be prepared as disclosed in U.S. Pat. Nos. 2,520,400 issued Aug. 29, 1950, to C. M. Himel et al. or 3,513,139, issued May 19, 1970, to A. Y. Coran et al.

EXAMPLE 1

Preparation of 4-ethylpropylamino-N-p chlorophenylthio-N-methyl-3,5-dinitrobenzenesulfonamide A 2.2 g (0.012 mol) sample of p-chlorophenylsulfenyl chloride was added dropwise to a cooled ($-5°$ C to 0° C) solution of 3.5 g (0.1 mol) 4-ethylpropylamino-N-methyl-3,5-dinitrobenzenesulfonamide and 1.1 g (0.014 mol) pyridine in 25 ml dichloromethane. The reaction was stirred for 20 minutes and then diluted with 50 ml dichloromethane, washed with water, washed with aqueous sodium bicarbonate solution, and dried over magnesium sulfate. The dichloromethane was then evaporated under reduced pressure to give a solid residue. Recrystallization from ethanol gave the product as red-orange plates, m.p. 89°–91° C. Elemental analysis for $C_{18}H_{21}ClN_4O_6S_2$ showed: % S, calc. 13.1, found 13.3; % Cl, calc. 7.3, found 7.8.

EXAMPLE 2

Preparation of 4-ethylpropylamino-N methylthio-N-methyl-3,5-dinitrobenzenesulfonamide A solution of 3.5 g (0.01 mol) 4-ethylpropylamino-N-methyl-3,5-dinitrobenzenesulfonamide, 1.1 g (0.014 mol) pyridine and 0.83 g. (0.012 mol) methylsulfenyl chloride in 25 ml dichloromethane was prepared at $-10°$ C and then stirred at 0° C until the 4-ethyl-propylamino-N-methyl-3,5-dinitrobenzenesulfonamide reactant could not be detected by thin layer chromatography on silica gel (benzene/acetone eluant). The reaction mixture was then washed with water, dried over magnesium sulfate and evaporated under reduced pressure to give an oily residue. The residue was crystallized from ethanol to give 2.7 g of the product, as yellow crystals, m.p. 92°–94° C. Elemental analysis for $C_{13}H_{20}N_4O_6S_2$ showed: % S, calc. 16.3, found 16.1.

EXAMPLE 3

Preparation of 4-dipropylamino-N methylthio-N-methyl-3,5-dinitrobenzenesulfonamide A 1.1 g (0.012 mol) sample of methylsulfenyl chloride was added dropwise to a cooled ($-5°$ to $-10°$ C) solution of 3.6 g (0.01 mol) 4-dipropylamino-N-methyl-3,5-dinitrobenzenesulfonamide and 1.1 g (0.014 mol) pyridine in 25 ml dichloromethane. The reaction mixture was then stirred at about 0° C until the sulfonamide reactant could not be detected by thin layer chromatography on silica gel (benzene/acetone eluant). The reaction mixture was then washed with water, dried over magnesium sulfate and evaporated under reduced pressue to give a yellow semi-solid residue. The residue was recrystallized from ethanol to give 2.3 g of the product, as a yellow solid, m.p. 119°–121° C. Elemental analysis for $C_{14}H_{22}N_4O_6S_2$ showed: % S, calc. 15.8, found 15.9.

UTILITY

The compounds of the invention have exhibited biological activity against a variety of organisms, particularly nematodes, when applied in biocidally effective amounts to such organisms.

The compounds of the invention are particularly effective killers of soil-dwelling nematodes — that is, the unsegmented roundworms of the class Nematoda, also known as eelworms, which customarily inhabit soil and feed upon the roots of plants growing therein. Included are the cyst forming nematodes of the genus Heterodera (e.g. the golden nematode bulb and stem nematodes of the genus Ditylenchus, the root knot nematodes of the genus Meloidogyne, the root-lesion nematodes of the genus Pratylenchus, the citrus nematod the genus Tylenchulus, the sting nematodes of the genus Balonolaimus, and the plant nematodes of such genera as Nacobus, Radopholus, and the like.

The compounds of the invention are employed for the destruction of nematodes in soil by disseminating the compounds in the nematode-infested soil, in nematocidally effective concentrations. The nematocidally effective concentrations in the soil lie within the range of from about 1 to about 500 parts per million, on a weight basis based on the weight of the air-dry soil, with the usual dosage ranging from about 4 to about 20 parts per million, on the same basis. As a practical matter, the effective dosage generally amounts to from about 1 to about 100 pounds of the nematocide per acre of land, depending upon the depth of soil to be treated, which may be up to 6, or 8, or even 12 inches, depending upon the particular species of plants and nematodes involved. Generally, dosages of from about 2 to about 40 pounds of the nematocide per acre of land are preferred.

Some of the compounds of the invention are solids at ordinary room temperature. These may be applied to the soil neat — as by grinding the solids, then admixing the resulting dust or powder with the soil to be treated. Alternatively, the compounds may be dissolved in a suitable liquid diluent and the solution applied to and mixed with the soil, or the compounds may be formulated with a suitable solid carrier and applied as a dust, powder or as granules to the soil and admixed therewith. By the use of suitable emulsifying and dispersing agents, the compounds can be emulsified and dispersed in water and the emulsion applied to the soil to be treated to provide effective control of the nematodes therein. Any of the usual emulsifying and dispersing agents commonly employed in forming aqueous emulsions and suspensions of water-insoluble materials can be used for this purpose. Generally only a small concentration of the emulsifying agents is required, as little as 0.05 percent of the weight of the final formulation being effective in many cases, while seldom will more than about 10% of the weight of the final formulation be required. Usually the concentration of the emulsifying or dispersing agent will be from about 0.5 to 5 percent of the weight of the formulation. Alternatively, or in addition, in some cases it may be to advantage to dissolve the compounds to be used in a solvent which can readily be dispersed in water to produce a heterogeneous dispersion of the nematocide in the water.

Where the compounds are to be applied as a solution, suitable solvents include alcohols, ketones and hydrocarbons, such as, for example, isopropyl alcohol, benzene, acetone, methyl ethyl ketone, secondary butyl alcohol, kerosene, chlorinated hydrocarbons, various non-phytotoxic hydrocarbon fractions which are ordinarily used in disseminating agricultural chemicals, including spray oils, horticultural oils, and the like.

The suitable solid carriers ordinarily are those which are essentially inert in the soil and which are not hygroscopic — for if they are hygroscopic the final formulation will not remain dry and free-flowing. In some cases, however, it may be desirable to employ as carrier a solid which is not inert as, for example, a solid fertilizer such as a commercial mixed solid fertilizer, rock phosphate, urea or the like. Suitable inert carriers are those well known to the art including the clays such as the kaolinites, the bentonites and the attapulgites; other minerals in natural state such as talc, pyrophyllite, quartz, diatomaceous earth, fuller's earth, chalk, rock phosphate and sulphur; and chemically modified minerals, such as acid washed bentonites, precipitated calcium phosphates, precipitated calcium carbonate, and colloidal silica. These diluents may represent a substantial portion; for example 50 to 98 percent by weight of the entire formulation.

These solid formulations can be prepared by grinding or airmilling the carrier and nematocide together. Alternatively, the solid formulations can be formed by dissolving the nematocide in a suitable solvent, such as a volatile solvent, impregnating and/or coating the particles with the solution and if necessary, removing the solvent. The formulaton also can be effected by melting the nematocide and mixing the molten nematocide with the carrier. Granular formulations can be prepared by impregnating and/or coating granules of the carrier with the nematocide or by forming granules of mixtures of the nematocide and carrier.

From the standpoint of mechanics, the nematocide, neat or as a formulation, is applied to the soil in any manner which enables an intimate admixture with the soil to be obtained. Thus the nematocide, which includes formulations thereof, can be applied to the surface of the soil, or it can be applied below the surface of the soil, and then admixed with the soil. If in the form of a liquid formulation, the nematocide can be drenched onto the surface of the soil or injected into the soil. Other conventional means, well known in the art, can be used to effect intimate admixture of the nematocide with the soil to be treated.

The formulations of the nematocides may also contain other materials, such as insecticides, fungicides, nematocides or different action and/or different physical characteristics, hormones, and/or fertilizers, to form multipurpose compositions.

EXAMPLE 4

Nematode Control

The compounds of the invention were tested for nematocidal activity by the following method: a 0.38 ml portion of a 3% acetone solution of the test compound was diluted with 1 ml acetone. The resulting solution was homogeneously mixed with 20 cc of vermiculite. The treated vermiculite was then mixed homogeneously with 750 g of soil, dry weight basis, which was severely infested with free-living nematodes (mixed culture of *Meloidogyne javanica* and *Meloidogyne incognita*). This mixing gave a concentration of approximately 15 parts of the test compound per million parts of soil. This treated soil was stored for 4 days at 65°-75° F. It was then divided equally into 3 parts, each of which was put into a separate pot and kept for another 3 days. A 3-week-old tomato (v. Bonny Best) seedling was then transplanted into each pot and incubated for 13 days under greenhouse conditions. After this period they were removed and the soil was washed from their roots. The nematocidal effectiveness of the test compound was determined by observing each plant for signs of nematode invasion (number of galls formed, stunting, etc.).

The results of these tests, reported as the average of the 3 replicates on a 0 to 100 basis — 0 indicating no effectiveness; 100 indicating complete effectiveness — are reported in Table I.

TABLE I

Compound of the formula

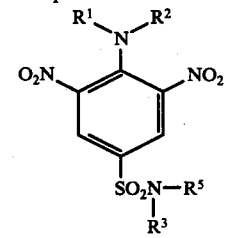

| Compound No. | $R^1$ | $R^2$ | $R^3$ | $R^5$ | Nematocidal Control % |
|---|---|---|---|---|---|
| 1 | $C_2H_5$ | n-$C_3H_7$ | $CH_3$ | $-S-\phi^*$-p-Cl | 69 |
| 2 | $C_2H_5$ | n-$C_3H_7$ | $CH_3$ | $-SCH_3$ | 97 |
| 3 | n-$C_3H_7$ | n-$C_3H_7$ | $CH_3$ | $-SCH_3$ | 88 |
| 4 | $C_2H_5$ | $C_2H_5$ | $CH_3$ | H | 0 |
| 5 | n-$C_3H_7$ | n-$C_3H_7$ | $CH_3$ | H | 0 |
| 6 | n-$C_3H_7$ | n-$C_3H_7$ | $C_2H_5$ | H | 0 |

*$\phi$ represents phenyl

What is claimed is:

1. A method for the control of nematodes which comprises applying to said nematodes a nematocidally effective amount of a compound of the formula

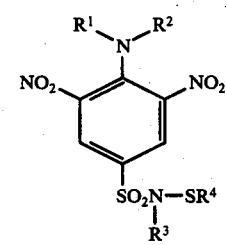

wherein $R^1$ is alkyl of 1 to 6 carbon atoms, $R^2$ is alkyl of 1 to 6 carbon atoms, $R^3$ is alkyl of 1 to 6 carbon atoms and $R^4$ is alkyl of 1 to 6 carbon atoms, haloalkyl of 1 to 2 carbon atoms and 1 to 5 of the same or different halogens selected from fluoro, chloro or bromo, or phenyl substituted with up to 2 fluoro, chloro, bromo or alkyl of 1 to 4 carbon atoms.

2. The method of claim 1 wherein $R^4$ is alkyl of 1 to 4 carbon atoms.

3. The method of claim 1 wherein $R^1$ is propyl, $R^2$ is propyl, $R^3$ is methyl and $R^4$ is methyl.

4. The method of claim 1 wherein $R^4$ is phenyl substituted with 1 to 2 fluoro, chloro, bromo or alkyl of 1 to 4 carbon atoms.

5. The method of claim 1 wherein $R^1$ is propyl, $R^2$ is propyl, $R^3$ is methyl and $R^4$ is p-chlorophenyl.

* * * * *